United States Patent
Hassing et al.

(10) Patent No.: US 9,514,277 B2
(45) Date of Patent: Dec. 6, 2016

(54) CLINICAL MONITORING NETWORK

(75) Inventors: Kai Hassing, Sindelfingen (DE);
Harald Greiner, Nufringen (DE)

(73) Assignee: KONINKLIJKE PHILIPS N.V.,
Eindhoven (NL)

( * ) Notice: Subject to any disclaimer, the term of this patent is extended or adjusted under 35 U.S.C. 154(b) by 2444 days.

(21) Appl. No.: 11/817,922

(22) PCT Filed: Mar. 6, 2006

(86) PCT No.: PCT/IB2006/050686
§ 371 (c)(1),
(2), (4) Date: Sep. 6, 2007

(87) PCT Pub. No.: WO2006/095299
PCT Pub. Date: Sep. 14, 2006

(65) Prior Publication Data
US 2010/0019910 A1    Jan. 28, 2010

(30) Foreign Application Priority Data
Mar. 8, 2005 (EP) .................................... 05101781

(51) Int. Cl.
*G08B 23/00* (2006.01)
*G06F 19/00* (2011.01)

(52) U.S. Cl.
CPC ....... *G06F 19/3412* (2013.01); *G06F 19/3406* (2013.01); *G06F 19/3418* (2013.01); *G06F 19/3456* (2013.01)

(58) Field of Classification Search
CPC ............. G06F 19/3412; G06F 19/3406; G06F 19/3456; G06F 19/3418

USPC ..................................... 340/500, 531, 539.1
See application file for complete search history.

(56) References Cited

U.S. PATENT DOCUMENTS

| | | | |
|---|---|---|---|
| 5,319,363 A | 6/1994 | Welch et al. | |
| 5,822,544 A * | 10/1998 | Chaco et al. | 705/2 |
| 5,942,986 A * | 8/1999 | Shabot et al. | 340/7.29 |
| 6,364,834 B1 * | 4/2002 | Reuss et al. | 600/300 |
| 6,402,691 B1 * | 6/2002 | Peddicord et al. | 600/300 |
| 2002/0138017 A1 * | 9/2002 | Bui et al. | 600/537 |
| 2003/0093103 A1 * | 5/2003 | Malackowski et al. | 606/170 |
| 2003/0109904 A1 * | 6/2003 | Silver et al. | 607/59 |
| 2003/0212311 A1 | 11/2003 | Nova et al. | |

(Continued)

OTHER PUBLICATIONS

Nelwan, et al., "Ubiquitous mobile access to real-time patient monitoring data", Computers in Cardiology 2002, vol. 29.

(Continued)

*Primary Examiner* — An T Nguyen

(57) ABSTRACT

A plurality of patient monitors (5, 6) which each monitor medical conditions of a patient and display text and graphs depicting such medical conditions are connected by a network (7) with a central station (4). Each monitor includes a paging unit (8) which communicates via the network with a paging server (3). In response to a monitor determining a critical event in its patient's monitored medical condition, a page event is sent via the network to the paging server (3). The paging server sends page messages to selective ones of the patient monitors, e.g., the monitors which are in closest proximity to a medical care professional associated with the patient, and the paging method is displayed by a display module (10) of the designated patient monitors.

10 Claims, 1 Drawing Sheet

(56) References Cited

U.S. PATENT DOCUMENTS

| | | | |
|---|---|---|---|
| 2004/0003412 A1* | 1/2004 | Halbert | 725/112 |
| 2004/0054261 A1* | 3/2004 | Kamataki et al. | 600/300 |
| 2004/0193449 A1* | 9/2004 | Wildman et al. | 705/2 |
| 2005/0027567 A1* | 2/2005 | Taha | 705/2 |
| 2005/0203892 A1* | 9/2005 | Wesley et al. | 707/3 |
| 2006/0167761 A1* | 7/2006 | Elcock et al. | 705/26 |

OTHER PUBLICATIONS

Nelwan, et al., "Ubiquitous mobile access to real-time patient monitoring data", Computers in Cardiology 1997.

* cited by examiner

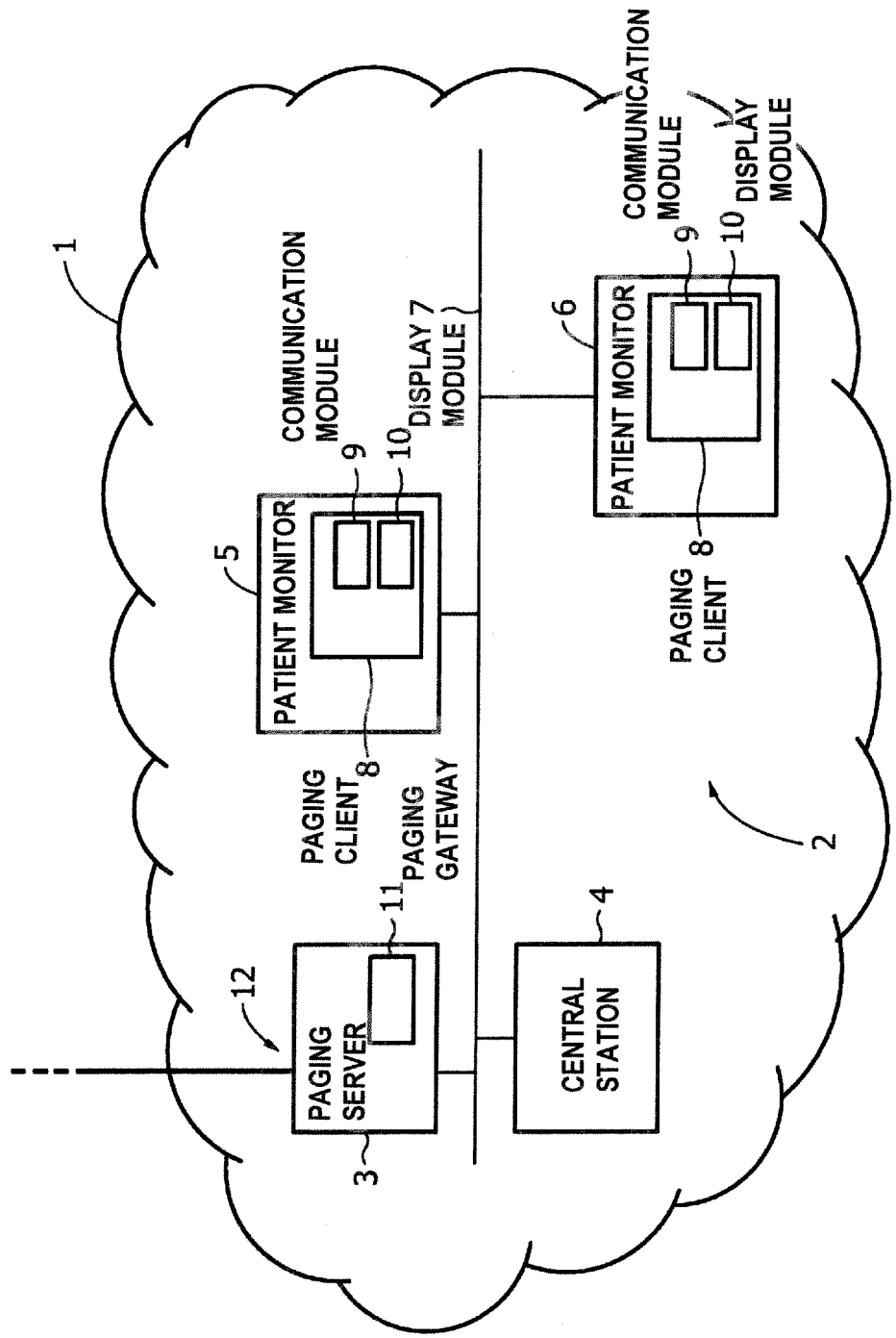

CLINICAL MONITORING NETWORK

The invention relates to a clinical monitoring network. Furthermore, the invention relates to a paging system, a computer program and a corresponding method.

Within a clinical monitoring network, it is an important feature to distribute alert information from the point of care, where the patient is monitored, to nurses and doctors within the clinical unit and/or other places in the hospital. When a patient has an alarm condition, the medical staff can be notified of this emergency. To notify medical staff about such alert conditions, two main technologies are known.

A first technology is based upon the idea to show real-time data windows, so called overview windows, for networked patients at a patient monitor. In the case of an alert, a first patient monitor merely shows data from a second, remote patient monitor. Such an overview window may open automatically, showing vital signs data (waves, numeric, alert messages) of the patient in alert in real-time. Here, typically restrictions exist regarding the number of parallel events that can be shown, the physical scope of the notification (because data is available at a limited number of stations only) and the configuration capabilities (e.g. which events are shown).

A second technology is based upon a paging system. From a central system in the network, alert information is collected, processed and forwarded to a separate, typically wireless, paging device. The paging system can be used for other, not alert-related information as well, e.g. drug therapy information or the like. Page events can be triggered either manually or automatically. For using this technology, the medical staff has to carry a separate piece of equipment, i.e. a pager.

From U.S. Pat. No. 6,364,834 B1, an integrated medical monitoring system is known, comprising at least one central monitor and at least one patient monitor, which are connected to each other through an integrated communications link. The central monitor is adapted to send information to a paging system, a personal digital assistant (PDA), a telephone, a laptop, a desktop or to another remote access device, which is also tied to the central station via the communication link.

It is an object of the present invention to provide an inexpensive solution to notify medical staff about a critical event at a point of care.

In accordance with one aspect, a clinical monitoring network includes a number of medical devices, wherein at least one medical device is adapted to implement the functionality of a paging client. In other words, the at least one medical device is adapted to serve as a paging client. A medical device according to the present invention is a device, apparatus, or system used for patient monitoring, treatment, or therapy, particularly without normally entering metabolic pathways. For the purposes of this document, the scope of medical devices is further limited to devices that provide support for electronic communications. This definition includes medical devices for remote patient monitoring, e.g. patient monitors, primary and secondary central stations, that are interconnected via a clinical monitoring network.

In accordance with another aspect, a paging system includes a paging server and a number of paging clients, wherein at least one paging client is a medical device attachable to a clinical monitoring network.

In accordance with another aspect, a computer program includes computer instructions to transmit a paging message from a paging server to a medical device attachable to a clinical monitoring network, the medical device serving as a paging client, when the computer program is executed in a computer.

In accordance with another aspect, a computer program includes computer instructions to adapt a medical device attachable to a clinical monitoring network to implement the functionality of a paging client, when the computer program is executed in a computer.

In accordance with another aspect, a medical device is attachable to a clinical monitoring network as a paging client.

In accordance with another aspect, a method includes the step of automatically transmitting a paging message in case of a critical event at a point of care, using a paging server and a number of paging clients, wherein at least one of the paging clients is a medical device attachable to a clinical monitoring network.

In accordance with another aspect, a pager client functionality is embedded in a medical device, in particular in a patient monitor, rather than using separate paging client hardware to be carried by the medical staff. The idea makes use of the fact that in most cases a large number of networked medical devices already exist within a clinical unit. In other words, the paging system according to the invention uses the medical devices, e.g. patient monitors, which are available in nearly every room of the hospital, to indicate page events and/or other information to clinical users.

With the embedded pager client functionality it is possible to conduct every function of a traditional paging system in a patient monitor, or other device, connected to a clinical monitoring network (which is typically a closed network system for real-time patient monitoring) and to optionally augment this functionality by allowing access to additional data already available in the system, using the information in the page event as a reference.

Thus, the total costs of notifying medical staff about a critical event at a point of care are reduced dramatically. At the same time the traditional paging functionality remains unchanged or is even enhanced.

By integrating the pager technology into a patient monitoring system or another clinical network, the information content is neither limited to the real-time data nor to short numeric or alphanumeric messages. In other words the paging client functionality of the medical device is used for distribution of information which is not typically available in a real-time patient monitoring system. Besides name and location of the patient, alert condition and priority, e.g. name and telephone number of a person responsible for the patient, care instructions or instructions to contact a specialist might be part of the paging message.

Additionally, an increase in the number of patients for which a remote notification of emergency conditions can be realized, because the number of patient monitors attached to the clinical network is not limited. In other words, every patient monitor connected to the network can be the source of a critical value of a clinical measurement parameter, causing the generation of a paging message.

In a traditional patient monitoring system, overview windows for remote patients can only be generated within a single subnet, i.e. within a group of patient monitors connected to the same central station of a clinical network. Clinical networks may comprise, however, a large number of central stations interconnected e.g. by means of a relay server. Furthermore, there might be several clinical networks connected to each other, forming e.g. a network covering several buildings or even several hospitals at different locations. Because the paging server can potentially interface to a very large number of separate clinical networks simultaneously, the present application provides remote alert capabilities for a much larger patient group than the traditional alert window technology.

The medical device and the gateway server and/or another component of the clinical monitoring network, e.g. a central station, is adapted to run a computer program comprising computer instructions adapted to perform different aspects when the computer program is executed in the computer. The technical effects can thus be realized on the basis of the instructions of the computer program. Such a computer program can be stored on a carrier such as a CD-ROM or it can be available over the Internet or another computer network. Prior to executing, the computer program is loaded into the computer by reading the computer program from the carrier, for example by means of a CD-ROM player, or from the internet, and storing it in the memory of the computer. The computer includes inter alia a central processor unit (CPU), a bus system, memory means, e. g. RAM or ROM, storage means, e. g. floppy disk or hard disk units and input/output units.

The present paging system can easily be implemented in traditional clinical monitoring networks, in particular traditional patient monitors, central stations and paging servers, by executing a software update of the operating or system software of these components.

The accompanying drawing is a schematic block diagram showing a clinical monitoring network according to the invention.

The clinical monitoring network 1 comprises a real-time patient monitoring system 2 and a paging server 3. The patient monitoring system 2 comprises a central station 4 as well as a first patient monitor 5 and a second monitor 6. Paging server 3, central station 4 and both patient monitors 5, 6 are connected to a network backbone 7. The network 1 may be implemented as wired or wireless network.

Each patient monitor 5, 6 incorporates a paging client 8. For this purpose, according computer software is executed in the built-in computers of the patient monitors. By means of this computer software the patient monitors 5, 6 are adapted to implement the paging client functionality.

The paging client 8 comprises a communication module 9 adapted to communicate with the paging server 3 and a display module 10 for visualizing the information sent by the paging server 3. The paging message or paging information, i.e. the data sent from the paging server 3 to the paging client 5, 6, can include textual information, reference pointers (e.g. to a specific patient or a specific care giver or to specific time/data) as well as graphical information (e.g. bitmap data representing a measurement signal) or even voice.

The paging server 3 comprises a paging gateway 11 for establishing communication between paging clients 5, 6 and the paging server 3. For this purpose, the paging gateway 11 utilizes the existing communication infrastructure, i.e. the real-time clinical network with its network backbone 7 for connecting the patient monitors 5, 6 to the paging server 3. No separate communication network between paging clients 8 and paging server 3 is required. In other words, the network used by the paging server 3 is the same network used to interconnect patient monitors 5, 6 with the central station 4. In the present embodiment, the paging gateway 11 is implemented as part of the paging server 3. However, the paging gateway 11 may as well be implemented as part of the central station 4 or as an external device. The paging gateway 11 and other parts of the paging server are preferably implemented as computer software. By means of this computer software the paging server 3 is adapted to transmit a paging message to the patient monitors 5, 6 via the central monitor 4 and the network backbone 7.

The system as described above can be used to inform clinical staff about emergency situations by sending a paging event as a result of an alarm condition for a first patient, detected by a first patient monitor 5, via the central station 4 and the paging server 3 to all paging clients 8 embedded in other patient monitors 6. A paging message is generated by the paging server 3 with regard to a predetermined or determined set of conditions. These conditions are stored in a database and are accessible by the paging server 3. For example, in case a critical event has been registered by means of the first patient monitor 5, the paging server 3 receives the event data from the patient monitor 5 via the central station 4. In a next step the paging server 3 determines, whether a certain set of conditions is fulfilled. This might be the case for example if a patient shows a high heart rate and an invalid EKG rhythm at the same time. If this set of conditions is fulfilled, the paging server 3 generates a paging message.

The paging message contains a predefined set of data, in accordance with the specific set of conditions. For example, in the above case the paging message includes the patient's name and location, the time-stamp of the event, the value for the heart rate with the exceeded limit and possibly an annotated EKG rhythm strip. The sets of data corresponding to the sets of conditions are stored in a database accessible by the paging server 3 The database might be hosted by a clinical information database system (not shown). It includes for example archived physiological data such as vital sign data, waveform data, events from the patient monitoring system and other data, for example demographics, assessments, diagnoses, care plans, notes, laboratory data, prescription and pharmacy information, insurance and billing information and/or other personal patient information.

Sending of the paging information is preferably triggered automatically, e.g. upon detection of an alarm condition. Alternatively, the sending of the paging information is triggered manually, e.g. when a nurse is looking for a physician who is currently treating patients in the clinical unit.

The alert paging information, which includes typically an alert description, a patient name and a patient location identifier, is preferably transmitted to all the paging clients 8 in all patient monitors 5, 6 by appropriate communication mechanisms, e.g. by confirmed messaging in a bi-directional communication system or by repeated transmission with a relatively low data transmission rate. The distribution of the paging messages may use broadcast, multicast or unicast messaging to address only a subset of the patient monitors. In a preferred embodiment of the invention, there is a configurable list of paging clients 5, 6 that should receive a paging event.

The paging clients 8 use specific user interface techniques to display the paging information in textual or graphical form. The paging information is preferably displayed in an automatic pop-up window, i.e. a temporary window that automatically opens when a page event is received, or in a dedicated permanent window in a reserved field on the screen of the patient monitor display. Sound and/or color and display attributes (e.g. blinking) might be used to further emphasize the information based on the urgency of the condition. Color coding for example can be used to indicate the severity of the received information. Typical colors for indicating patient alerts related to a remote patient are red and yellow.

Preferably, multiple paging information entries are shown simultaneously. If the number of paging events exceeds the available display space, multiple paging information entries are shown alternately, e.g. in the form of a smoothly scrolling ticker band.

To ensure readability from a distance, preferably only a limited amount of information is displayed, including patient name or patient identifier, paging text, patient location etc. Preferably, the paging clients 8 cause the patient monitors 5, 6 to open a relatively large window, showing the patient name and/or location and an alarm text. Thus, the clinical staff can quickly identify the source and severity of the alarm, even if they are not standing right next to the patient monitor. For the alert ticker, the central station 4 and/or paging server 3 may refresh the list of active alerts in the network periodically so that patient monitors 5, 6 and medical devices that have just been switched on also show the same list.

In a special embodiment, the patient monitors 5, 6 hold a history of alert page events and present this history in the form of a static or dynamic (scrolling) window or in the form of an alert ticker, so that a certain number of recent page events can be seen in parallel by the clinical user.

From the information shown in the pager window on the patient monitor 5, 6 it is possible for the clinical user to access further information provided by the pager server 3 or, alternatively, to access further information from other systems by referencing an identification of the paging event or an identification of the patient referenced in the paging event. The clinical user can establish a network connection, e.g. by selecting the paging event on the screen of the patient monitor 5, 6. Using the network connection, real-time patient information can be showed as acquired by the patient monitor 5, 6 used for that particular patient, e.g. in the form of a traditional remote viewing window. Thus, it is possible to obtain a larger number of up-to-date information items to assess the patient's condition from a remote location.

The configuration of the central station 4 and/or the paging server 3 includes, among others: the specific events forwarded to the paging client 8, the specific clients or patient monitors 5, 6 that are notified and the audible signals generated at the patient monitor 5, 6. The configuration of the specific clients that are to be notified is preferably carried out using known concepts at the central station 4 to group the patients in care groups. For each care group specific nurses and/or doctors are responsible.

Preferably, the distribution of other information to the paging client 8 is supported. Such other information includes: staff notification about new patients arriving, second level alarms calculated by connected information systems, results from blood analysis etc., such augmenting the capabilities of the patient monitors 5, 6.

In a preferred embodiment, the paging client function is additionally or solely embedded in other medical devices directly attached to the wireless or wired clinical monitoring network 1, such as primary and secondary central stations, etc. (not shown). An example of secondary central stations are units located at a openly visible place, e.g. in the form of hallway display units.

The paging server 3 is preferably adapted to coexist with a standard paging system (not shown) by distributing the paging information simultaneously to both the standard paging devices using an external interface 12 and to the paging clients 8 embedded in devices attached to the clinical monitoring network 1. Furthermore, the paging server 3 is also adapted to receive data from a standard radio paging system via the external interface 12 and forward any paging events received in this system via the paging gateway 11 to any configured paging clients 8 on the real-time clinical network 1.

Preferably, the paging message is transmitted to a limited number of paging clients. If location tracking of clinical staff is supported, e.g. by means of a location system, e.g. an indoor positioning system, the location of a number of addressees is determined beforehand and the selection of patient monitors 5, 6 and/or other medical devices to which the page event is distributed is automatically limited to devices which are known to be in the proximity of the clinical user(s) who need to receive the page event. In this case, for each paging message a number of identifiers are created, indicating the desired destination(s) and/or user(s).

Preferably, the pager client 8 comprises a user interface adapted (not shown) to allow a clinical user to actively confirm that the paging information was received. To acknowledge the paging message a button on a touch screen may be pressed or an identification number is entered by means of the user interface, either manually or automatically.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. It will furthermore be evident that the word "comprising" does not exclude other elements or steps, that the words "a" or "an" do not exclude a plurality, and that a single element, such as a computer system or another unit, may fulfil the functions of several means recited in the claims. Any reference signs in the claims shall not be construed as limiting the claim concerned.

REFERENCE LIST 1 clinical monitoring network
2 patient monitoring network
3 paging server
4 central station
5 first patient monitor
6 second patient monitor
7 network backbone
8 paging client
9 communication module
10 display module
11 paging gateway
12 external interface

The invention claimed is:

1. A clinical monitoring network comprising:
a network backbone;
a central station connected with the network backbone;
a plurality of medical devices including a plurality of patient monitors, each patient monitor:
monitors physiological conditions of a corresponding patient,
displays representations of the physiological conditions of the corresponding patient on a physiological display, communicates the monitored physiological conditions and critical event conditions with the central station via the network backbone, includes a paging display module;

a paging server connected with the network backbone to receive at least the communicated critical event conditions concerning a first patient whose physiological conditions are monitored by a first of the patient monitors and to communicate paging messages to selected patient monitors other than or in addition to the first patient monitor;

wherein the display modules of the patient monitors receive the paging messages communicating critical event conditions concerning other patients and display the paging messages on the physiological display in addition to the displayed representations of the monitored physiological conditions of the corresponding monitored patient such that at least some of the patient monitors display the monitored physiological condition representations of one patient and paging messages communicating the critical event conditions concerning one or more other patients;

wherein the paging display module displays the paging information of the one or more other patients in a pop-up window on the physiological display.

2. The clinical monitoring network as claimed in claim 1, wherein said displayed paging message includes graphical and textual representations depicting the physiological conditions of the one or more other patients not previously displayed on the physiological display.

3. The clinical monitoring network as claimed in claim 1, wherein said paging message includes a scrolling ticker band which shows paging information relating to a plurality of the other patients.

4. The clinical monitoring network as claimed in claim 1, further including:

a plurality of secondary stations positioned in openly visible places, each secondary station having a paging message display.

5. The clinical monitoring network as claimed in claim 1, wherein the patient monitor includes a touch screen on which the physiological condition representations of the one patient and the paging messages concerning the one more other patients are displayed which touch screen is touched to acknowledge the displayed paging messages.

6. The clinical monitoring network as claimed in claim 1, wherein the page messages include archived information from a clinical information database.

7. The clinical monitoring network as claimed in claim 1, further including:

with the paging server, sending the page message via the network to at least one secondary station which does not monitor medical conditions of a corresponding patient and which is positioned in an openly visible place; and displaying the page message on the secondary station.

8. The clinical monitoring network as claimed in claim 1, further including:

retrieving information about the first patient from a clinical information database;

incorporating the retrieved information into the page message that is displayed on one of the selected patient monitors other than or in addition to the first patient monitor.

9. The clinical monitoring network as claimed in claim 1, wherein displaying the page message includes displaying the page message in textual or graphic form in a pop-up window on one of the selected patient monitors other than or in addition to the first patient monitor.

10. The clinical monitoring network as claimed in claim 1, wherein the displayed paging messages include care instructions.

* * * * *